United States Patent
Okoniewski

(10) Patent No.: US 8,932,213 B2
(45) Date of Patent: Jan. 13, 2015

(54) SEAL ANCHOR WITH NON-PARALLEL LUMENS

(71) Applicant: Covidien LP, Mansfield, MA (US)

(72) Inventor: Gregory Okoniewski, North Haven, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/248,534

(22) Filed: Apr. 9, 2014

(65) Prior Publication Data

US 2014/0221758 A1    Aug. 7, 2014

Related U.S. Application Data

(63) Continuation of application No. 14/248,520, filed on Apr. 9, 2014, which is a continuation of application No. 13/891,717, filed on May 10, 2013, which is a continuation of application No. 12/887,847, filed on Sep. 22, 2010.

(60) Provisional application No. 61/247,654, filed on Oct. 1, 2009.

(51) Int. Cl.
*A61B 1/32* (2006.01)
*A61M 13/00* (2006.01)
*A61B 17/34* (2006.01)
*A61B 17/02* (2006.01)
*A61B 17/00* (2006.01)

(52) U.S. Cl.
CPC .......... *A61M 13/003* (2013.01); *A61B 17/3423* (2013.01); *A61B 17/3462* (2013.01); *A61B 17/0218* (2013.01); *A61B 17/3498* (2013.01); *A61B 2017/3429* (2013.01); *A61B 2017/3445* (2013.01); *A61B 2017/3466* (2013.01); *A61B 2017/3492* (2013.01); *A61B 2017/00238* (2013.01); *A61M 2202/02* (2013.01)
USPC ............ 600/205; 600/201; 600/206; 600/208

(58) Field of Classification Search
USPC .................................. 600/201–235, 245–246
See application file for complete search history.

(56) References Cited

U.S. PATENT DOCUMENTS

| | | |
|---|---|---|
| 4,016,884 A | 4/1977 | Kwan-Gett |
| 4,112,932 A | 9/1978 | Chiulli |
| 4,183,357 A | 1/1980 | Bentley et al. |

(Continued)

FOREIGN PATENT DOCUMENTS

| | | |
|---|---|---|
| EP | 0807416 A2 | 11/1997 |
| EP | 0950376 A1 | 10/1999 |

(Continued)

OTHER PUBLICATIONS

European Search Report for corresponding EP 10251693 date of mailing is Feb. 22, 2011.

*Primary Examiner* — Jan Christopher Merene

(57) ABSTRACT

A seal anchor member defines a housing defining a longitudinal axis, the housing having leading and trailing ends, and including a plurality of lumens extending between the leading and trailing ends, each lumen being adapted for substantially sealed reception of an object therein and defining a longitudinal axis, wherein at least two of the lumens define longitudinal axes that are non-parallel to facilitate angled, at-rest placement of multiple instruments within the seal anchor member.

7 Claims, 4 Drawing Sheets

(56) References Cited

U.S. PATENT DOCUMENTS

| | | |
|---|---|---|
| 4,402,683 A | 9/1983 | Kopman |
| 4,653,476 A | 3/1987 | Bonnet |
| 4,863,430 A | 9/1989 | Klyce et al. |
| 4,863,438 A | 9/1989 | Gauderer et al. |
| 5,073,169 A | 12/1991 | Raiken |
| 5,082,005 A | 1/1992 | Kaldany |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,312,391 A | 5/1994 | Wilk |
| 5,330,486 A | 7/1994 | Wilk |
| 5,334,143 A | 8/1994 | Carroll |
| 5,345,927 A | 9/1994 | Bonutti |
| 5,366,478 A | 11/1994 | Brinkerhoff et al. |
| 5,375,588 A | 12/1994 | Yoon |
| 5,391,156 A | 2/1995 | Hildwein et al. |
| 5,395,367 A | 3/1995 | Wilk |
| 5,437,683 A | 8/1995 | Neumann et al. |
| 5,460,170 A | 10/1995 | Hammerslag |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,522,791 A | 6/1996 | Leyva |
| 5,524,644 A | 6/1996 | Crook |
| 5,540,648 A | 7/1996 | Yoon |
| 5,545,179 A | 8/1996 | Williamson, IV |
| 5,601,581 A | 2/1997 | Fogarty et al. |
| 5,634,911 A | 6/1997 | Hermann et al. |
| 5,634,937 A | 6/1997 | Mollenauer et al. |
| 5,649,550 A | 7/1997 | Crook |
| 5,651,771 A | 7/1997 | Tangherlini et al. |
| 5,653,705 A | 8/1997 | de la Torre et al. |
| 5,672,168 A | 9/1997 | de la Torre et al. |
| 5,683,378 A | 11/1997 | Christy |
| 5,685,857 A | 11/1997 | Negus et al. |
| 5,713,858 A | 2/1998 | Heruth et al. |
| 5,713,869 A | 2/1998 | Morejon |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A * | 5/1999 | Gilson .................. 606/213 |
| 5,906,577 A | 5/1999 | Beane et al. |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A | 8/2000 | Macoviak et al. |
| 6,110,154 A | 8/2000 | Shimomura et al. |
| 6,142,936 A | 11/2000 | Beane et al. |
| 6,183,485 B1 | 2/2001 | Thomason et al. |
| 6,197,002 B1 | 3/2001 | Peterson |
| 6,217,555 B1 | 4/2001 | Hart et al. |
| 6,228,063 B1 | 5/2001 | Aboul-Hosn |
| 6,238,373 B1 | 5/2001 | de la Torre et al. |
| 6,241,768 B1 | 6/2001 | Agarwal et al. |
| 6,254,534 B1 | 7/2001 | Butler et al. |
| 6,264,604 B1 | 7/2001 | Kieturakis et al. |
| 6,315,770 B1 | 11/2001 | de la Torre et al. |
| 6,319,246 B1 | 11/2001 | de la Torre et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,488,620 B1 | 12/2002 | Segermark et al. |
| 6,488,692 B1 | 12/2002 | Spence et al. |
| 6,527,787 B1 | 3/2003 | Fogarty et al. |
| 6,551,270 B1 | 4/2003 | Bimbo et al. |
| 6,558,371 B2 | 5/2003 | Dorn |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,706,050 B1 | 3/2004 | Giannadakis |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,814,078 B2 | 11/2004 | Crook |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,100,614 B2 | 9/2006 | Stevens et al. |

(56) References Cited

U.S. PATENT DOCUMENTS

| | | |
|---|---|---|
| 7,101,353 B2 | 9/2006 | Lui et al. |
| 7,153,261 B2 | 12/2006 | Wenchell |
| 7,163,510 B2 | 1/2007 | Kahle et al. |
| 7,192,436 B2 | 3/2007 | Sing et al. |
| 7,195,590 B2 | 3/2007 | Butler et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,084 B2 | 6/2007 | Skakoon et al. |
| 7,238,154 B2 | 7/2007 | Ewers et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,393,322 B2 | 7/2008 | Wenchell |
| 7,412,977 B2 | 8/2008 | Fields et al. |
| 7,445,597 B2 | 11/2008 | Butler et al. |
| 7,473,221 B2 | 1/2009 | Ewers et al. |
| 7,540,839 B2 | 6/2009 | Butler et al. |
| 7,559,893 B2 | 7/2009 | Bonadio et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,847 B2 | 5/2010 | Smith |
| 7,727,146 B2 | 6/2010 | Albrecht et al. |
| 7,736,306 B2 | 6/2010 | Brustad et al. |
| 7,753,901 B2 | 7/2010 | Piskun et al. |
| 7,798,898 B2 | 9/2010 | Luciano, Jr. et al. |
| 8,317,690 B2 | 11/2012 | Ransden et al. |
| 2001/0037053 A1 | 11/2001 | Bonadio et al. |
| 2002/0038077 A1 | 3/2002 | de la Torre et al. |
| 2002/0183594 A1 | 12/2002 | Beane et al. |
| 2003/0014076 A1 | 1/2003 | Mollenauer et al. |
| 2003/0028179 A1* | 2/2003 | Piskun ................ 606/1 |
| 2003/0135091 A1 | 7/2003 | Nakazawa et al. |
| 2003/0171713 A1* | 9/2003 | McFarlane ................ 604/93.01 |
| 2003/0236549 A1 | 12/2003 | Bonadio et al. |
| 2004/0049099 A1 | 3/2004 | Ewers et al. |
| 2004/0092795 A1 | 5/2004 | Bonadio et al. |
| 2004/0092796 A1 | 5/2004 | Butler et al. |
| 2004/0111061 A1 | 6/2004 | Curran |
| 2004/0138529 A1 | 7/2004 | Wiltshire et al. |
| 2004/0167543 A1 | 8/2004 | Mazzocchi et al. |
| 2004/0267096 A1 | 12/2004 | Caldwell et al. |
| 2005/0020884 A1 | 1/2005 | Hart et al. |
| 2005/0043592 A1 | 2/2005 | Boyd et al. |
| 2005/0096695 A1* | 5/2005 | Olich ................ 606/213 |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0241647 A1 | 11/2005 | Nguyen et al. |
| 2005/0288558 A1 | 12/2005 | Ewers et al. |
| 2006/0020241 A1 | 1/2006 | Piskun et al. |
| 2006/0084842 A1 | 4/2006 | Hart et al. |
| 2006/0129165 A1 | 6/2006 | Edoga et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0229501 A1 | 10/2006 | Jensen et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0258899 A1 | 11/2006 | Gill et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0149859 A1 | 6/2007 | Albrecht et al. |
| 2007/0151566 A1 | 7/2007 | Kahle et al. |
| 2007/0156023 A1 | 7/2007 | Frasier et al. |
| 2007/0185387 A1 | 8/2007 | Albrecht et al. |
| 2007/0203398 A1 | 8/2007 | Bonadio et al. |
| 2007/0208312 A1* | 9/2007 | Norton et al. ................ 604/284 |
| 2008/0027476 A1 | 1/2008 | Piskun |
| 2008/0200767 A1 | 8/2008 | Ewers et al. |
| 2008/0255519 A1 | 10/2008 | Piskun et al. |
| 2009/0012477 A1 | 1/2009 | Norton et al. |
| 2009/0036745 A1 | 2/2009 | Bonadio et al. |
| 2009/0093752 A1* | 4/2009 | Richard et al. ................ 604/24 |
| 2009/0131751 A1 | 5/2009 | Spivey et al. |
| 2009/0221966 A1 | 9/2009 | Richard |
| 2009/0270685 A1 | 10/2009 | Moreno et al. |
| 2009/0326332 A1 | 12/2009 | Carter |
| 2010/0081880 A1 | 4/2010 | Widenhouse et al. |
| 2010/0185057 A1 | 7/2010 | Stearns et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0240960 A1 | 9/2010 | Richard |
| 2010/0249526 A1 | 9/2010 | Shelton, IV et al. |
| 2011/0015491 A1 | 1/2011 | Ravikumar et al. |
| 2011/0082341 A1 | 4/2011 | Kleyman et al. |
| 2011/0190590 A1 | 8/2011 | Wingardner, III et al. |

FOREIGN PATENT DOCUMENTS

| | | |
|---|---|---|
| EP | 1312318 A1 | 5/2003 |
| EP | 1774918 A1 | 4/2007 |
| EP | 2044889 A1 | 4/2009 |
| WO | 93/14801 | 8/1993 |
| WO | 94/04067 | 3/1994 |
| WO | 96/36283 | 11/1996 |
| WO | 97/33520 | 9/1997 |
| WO | 97/42889 | 11/1997 |
| WO | 99/16368 | 4/1999 |
| WO | 00/32120 | 6/2000 |
| WO | 01/49363 | 7/2001 |
| WO | 02/07611 | 1/2002 |
| WO | 2006/100658 A2 | 9/2006 |
| WO | 2008/015566 A2 | 2/2008 |
| WO | 2008/042005 | 4/2008 |
| WO | 2008/093313 | 8/2008 |
| WO | 2008/103151 | 8/2008 |
| WO | 2008/121294 A1 | 10/2008 |

* cited by examiner

SEAL ANCHOR WITH NON-PARALLEL LUMENS

CROSS-REFERENCE TO RELATED APPLICATIONS

This application is a continuation of U.S. patent application Ser. No. 14/248,520 filed Apr. 9, 2014, which is a continuation of U.S. patent application Ser. No. 13/891,717 filed May 10, 2013, which is a continuation of U.S. patent application Ser. No. 12/887,847 filed Sep. 22, 2010, which claims benefit of U.S. Provisional Application No. 61/247,654 filed Oct. 1, 2009, and the disclosures of each of the above-identified applications are hereby incorporated by reference in their entirety.

BACKGROUND

1. Technical Field

The present disclosure relates to a seal for use in a surgical procedure. More particularly, the present disclosure relates to a seal anchor member adapted for insertion into an incision in tissue and including a plurality of non-parallel lumens adapted for the sealed reception of one or more surgical objects such that a substantially fluid-tight seal is formed with both the tissue and the surgical object or objects.

2. Background of the Related Art

Today, many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

During a typical minimally invasive procedure, surgical objects, such as surgical access devices (e.g., trocar and cannula assemblies) or endoscopes, are inserted into the patient's body through an incision in tissue. In general, prior to the introduction of the surgical object or instrument into the patient's body, insufflation gasses are used to enlarge the area surrounding the target surgical site to create a larger, more accessible work area. Accordingly, the maintenance of a substantially fluid-tight seal is desirable so as to prevent the escape of the insufflation gases and the deflation or collapse of the enlarged surgical site.

To this end, various valves and seals are used during the course of minimally invasive procedures and are widely known in the art. Various seals have been developed including lumens for the reception of surgical instruments. Depending upon the needs of a particular surgical procedure, instruments may need to be angled with respect to one another for extended periods of time. Holding the instruments at angles with respect to one another and/or overcoming the internal biases of the seal anchor member through which the instruments are inserted may fatigue the surgeon and/or breach the fluid-tight barrier between the seal anchor member and surrounding tissue.

Accordingly, a continuing need exists for new seal anchor members that can be inserted directly into the incision in tissue and that can accommodate a variety of surgical objects or instruments while maintaining the integrity of an insufflated workspace.

SUMMARY

Disclosed herein is a seal anchor member including a housing including leading and trailing ends, and one or more lumens extending therethrough. Each of the lumens is adapted for receiving a surgical instrument in a substantially sealed reception. The one or more lumens are angled with respect to a longitudinal axis of the housing. At least two of the lumens define axes that are non-parallel with respect to one another. In an embodiment, the housing may include a plurality of lumens, e.g., three lumens, in which one of the lumens is parallel with respect to the longitudinal axis and the other two lumens are non-parallel with respect to each other and the longitudinal axis. As described herein, the lumens, while defining axes that are intersecting, do not cross each other since the lumens are laterally spaced apart, e.g., the axes, not the lumens, are intersecting when the housing is viewed in a side cross-sectional view. This arrangement of the lumens facilitates the simultaneous, non-parallel placement of multiple surgical objects or instruments within the seal anchor member. However, in other embodiments, the lumens may be intersecting.

Furthermore, the lumens may define openings at the leading end that are radially spaced apart about the trailing end. Alternatively, the lumens may define openings at the leading end that are spaced along a diameter of the trailing end. The openings defined by the lumens may be staggered about an axis of the trailing end or may be positioned along a diameter but offset from that diameter. Alternatively, the openings defined by the lumens may be positioned on a chord or a diameter of the trailing end.

The housing may be formed from a compressible material to facilitate adjusting the angles between instruments inserted within the lumens and with respect to the longitudinal axis of the housing. In the absence of a force, e.g, a radial force, upon the instruments inserted within the lumens, the lumens are angled, i.e., non-parallel, with respect to each other. During use, the angles of the lumens are adjustable by applying a force.

The leading end may include a groove, cut-out, or recess that is positioned adjacent to the proximal end of at least one of the lumens. The groove is configured and adapted to facilitate the insertion of the instrument into the lumen by stabilizing the instrument and leading the instrument into the lumen. The groove may be generally arcuate. The groove may narrow from the proximal end to the distal end of the groove. The groove may extend radially outward from the proximal end of the at least one lumen.

Furthermore, the housing of the seal anchor may be adapted to transition between a first compressed condition to facilitate at least partial insertion of the seal anchor member within a tissue tract, and a second expanded condition to facilitate securing of the seal anchor member within the tissue tract and in substantial sealed relation with tissue surfaces defining the tissue tract. In an embodiment, the housing may be formed from a compressible material or from a foam material. In an embodiment, the foam material may be at least partially constituted of a material selected from the group consisting of polyisoprene, urethane, and silicone. In another embodiment, the housing may be formed from a gel material.

The housing may also define a substantially arcuate configuration. The housing may define a substantially hour glass shape. Furthermore, the lumens may define openings at the leading end that are radially spaced apart about the trailing end. Alternatively, the lumens may define openings at the leading end that are spaced along a diameter of the trailing end. The openings defined by the lumens may be staggered about an axis of the trailing end or may be positioned along a diameter but offset from that diameter. Alternatively, the openings defined by the lumens may be positioned on a chord or a diameter of the trailing end.

These and other features of the apparatus disclosed herein will become more readily apparent to those skilled in the art from the following detailed description of various embodiments of the present disclosure.

BRIEF DESCRIPTION OF THE DRAWINGS

Various embodiments of the present disclosure are described hereinbelow with references to the drawings, wherein.

DETAILED DESCRIPTION OF THE EMBODIMENTS

Figure 1:
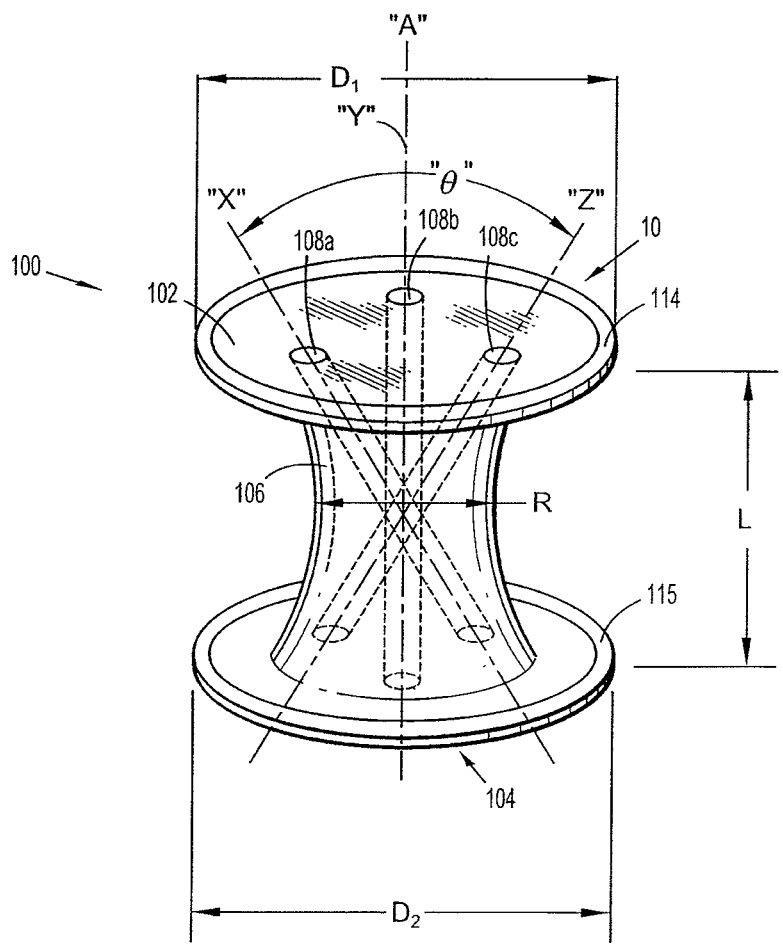
FIG. 1 is a front perspective view of a seal anchor in accordance with the present disclosure shown relative to tissue.
Figure 1:
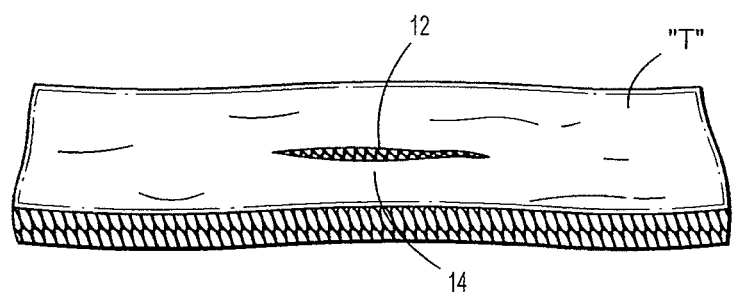

In the drawings and in the description which follows, in which like references numerals identify similar or identical elements, the term "proximal" will refer to the end of the apparatus which is closest to the clinician during use, while the term "distal" will refer to the end which is furthest from the clinician, as is traditional and known in the art. A seal anchor for use in a surgical procedure is shown and described in U.S. Pat. Pub. 2009-0093752, the entire contents of which are hereby incorporated by reference. The seal anchor member may be used during a minimally invasive procedure in which the seal anchor is inserted into an incision. Alternatively, the seal anchor may be used through a naturally occurring opening (e.g., anus or vagina) or any incision in a patient's skin.

The use and function of seal anchor member 100 will be discussed during the course of a typical minimally invasive procedure. Initially, the peritoneal cavity (not shown) is insufflated with a suitable biocompatible gas such as, e.g., $CO_2$ gas, such that the cavity wall is raised and lifted away from the internal organs and tissue housed therein, providing greater access thereto. The insufflation may be performed with an insufflation needle or similar device, as is conventional in the art. Either prior or subsequent to insufflation, a tissue tract 12 is created in tissue "T", the dimensions of which may be varied dependent upon the nature of the procedure.

A seal anchor 100 will now be described with reference to FIGS. 1 and 2. The seal anchor 100 defines a longitudinal axis "A" and has respective trailing (or proximal) and leading (or distal) ends 102, 104 and an intermediate portion 106 disposed between the trailing and leading ends 102, 104. Seal anchor member 100 includes one or more lumens (or ports) 108a, 108b, 108c disposed between the trailing and leading ends 102, 104 that define corresponding longitudinal axes "X", "Y", "Z". As seen in FIG. 1, the axes "X", "Y", "Z" defined by the lumens 108a, 108b, 108c, respectively, are non-parallel with respect to one another. To facilitate the simultaneous placement of instruments into each of the lumens 108a, 108b, 108c, the lumens 108a-c do not cross one another. The lumens 108a-c are laterally spaced apart such that, although the lumens 108a-c are angled with respect to one another, the lumens 108a-c do not intersect one another. In other embodiments, however, lumens may be arranged to cross one another. In contrast to seal anchor 100, a seal anchor 90 having parallel, non-intersecting lumens 98 is illustrated in FIG. 2A.

Figure 2A:
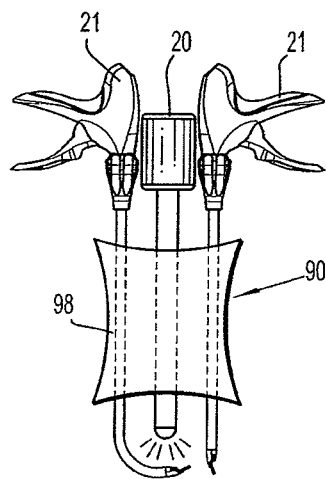
FIG. 2A is a front perspective view of a seal anchor member having lumens therein that are parallel to one another.
Figure 2B:
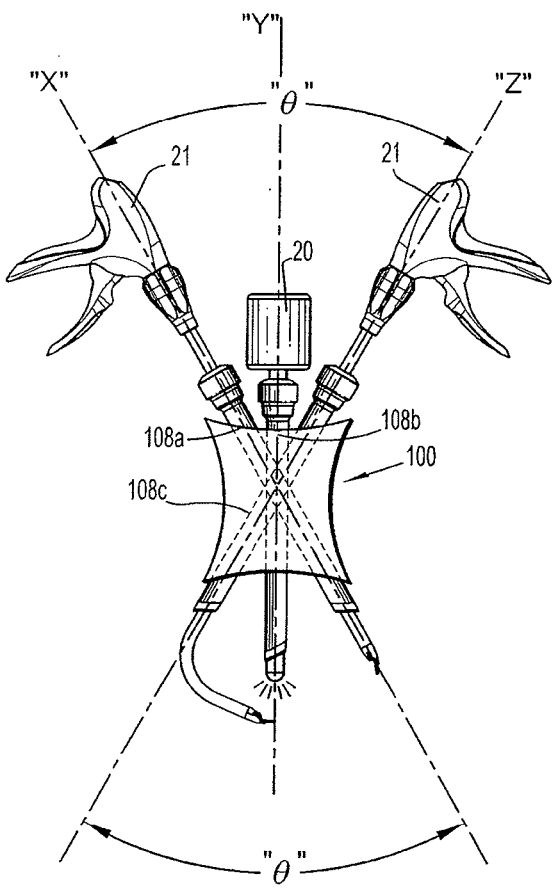
FIG. 2B is a front perspective view of the seal anchor of FIG. 1 shown with medical instruments inserted therein.

As seen in FIG. 2B, the lumens 108a-c are adapted to receive instrumentation therein in a substantially sealed manner. The lumens 108a-c are adapted to inhibit the escape of insufflation gasses within a body cavity with or without instrumentation being inserted therein. Accordingly, the lumens 108a-c have diameters that are adapted to contract in the absence of a surgical instrument inserted therein and are adapted to expand to accommodate instrumentation in a substantially sealed manner.

As shown in FIG. 2B, the instrumentation inserted within the lumens 108 may include, but are not limited to, a camera 20 that may be inserted within one of the lumens 108 and a pair of surgical instruments 21 that are inserted into two of the other lumens 108. Since the axes "X" and "Z" of the two lumens 108a, 108c, through which the pair of surgical instruments 21 are inserted, cross one another, the distance between the distal ends of the surgical instruments 21 is greater than it would be if the axes "X", "Z" were parallel to one another. Since the lumens 108a, 108c define non-parallel axes, manipulation of the surgical instruments 21 is facilitated since there is a lesser probability of the instruments 21 interfering with each other's use. Furthermore, since the at-rest state for the lumens 108a-c is at angles with respect to one another, surgeon fatigue is reduced for those procedures necessitating such positioning for an extended duration of time. Adjustment of the angles of the lumens with respect to one another is facilitated by overcoming the internal biasing force of the seal anchor member 100 by applying a radial force to the surgical instrumentation placed within the lumens 108a-c.

As previously discussed, FIG. 2A illustrates a seal anchor 90 including lumens 98 that are parallel to one another. Inserted within lumens 98 are surgical instruments 21 and camera 20. As seen in FIG. 2A, the parallel configuration of the lumens 98 hinder camera 20 in obtaining a clear view of the surgical site. It will be appreciated that the non-parallel, intersecting configuration of the lumens 108a-c of seal anchor 100 facilitate obtaining a lesser obstructed field of view than would be obtainable using seal anchor 90. In particular, as shown in FIG. 2B, axes "X" and "Z" define an angle "θ" therebetween. The greater the value of angle "θ", the lesser the probability of surgical instruments 21 obstructing the view of camera 20. Moreover, the greater the angle "θ", the lesser the probability of interference between instruments 21 during the procedure. In addition, the greater the angle "θ", the greater the number of internal structures included within the surgical field and within reach of instruments 21.

Proximal end 102 of seal anchor member defines a first diameter $D_1$ and distal end 104 defines a second diameter $D_2$. In one embodiment of seal anchor member 100, the respective first and second diameters $D_1$, $D_2$ of the proximal and distal ends 102, 104 are substantially equivalent, as seen in FIG. 1, although an embodiment of seal anchor member 100 in which diameters $D_1$, $D_2$ are different is also within the scope of the present disclosure. As depicted in FIG. 1, proximal and distal ends 102, 104 define substantially planar surfaces. However, embodiments are also contemplated herein in which either or both of proximal and distal ends 102, 104, respectively, define surfaces that are substantially arcuate to assist in the insertion of seal anchor member 100 within a tissue tract 12 defined by tissue surfaces 14 and formed in tissue "T", e.g., an incision, as discussed in further detail below.

Intermediate portion 106 defines a radial dimension "R" and extends longitudinally between proximal and distal ends 102, 104, respectively, to define an axial dimension or length "L". The radial dimension "R" of intermediate portion 106 varies along the axial dimension, or length, "L" thereof. Accordingly, seal anchor member 100 defines a cross-sectional dimension that varies along its length "L", which facilitates the anchoring of seal anchor member 100 within tissue "T", as discussed in further detail below. However, an embodiment of seal anchor member 100 in which the radial dimension "R" remains substantially uniform along the axial dimension "L" thereof is also within the scope of the present disclosure.

The radial dimension "R" of intermediate portion 106 is appreciably less than the respective diameters $D_1$, $D_2$ of proximal and distal ends 102, 104 such that seal anchor member 100 defines an "hour-glass" shape or configuration to assist in anchoring seal anchor member 100 within tissue "T", as discussed in further detail below. However, in an alternate embodiment, the radial dimension "R" of intermediate portion 106 may be substantially equivalent to the respective diameters $D_1$, $D_2$ of proximal and distal ends 102, 104. In cross section, intermediate portion 106 may exhibit any suitable configuration, e.g., substantially circular, oval or oblong.

The seal anchor 100 may be adapted to transition from an expanded condition to a compressed condition so as to facilitate the insertion and securement thereof within tissue tract 12 in tissue "T". In the expanded condition, seal anchor 100 is at rest and the respective radial dimensions $D_1$, $D_2$ of the proximal and distal ends 102, 104 of seal anchor 100, as well as the radial dimension R of the intermediate portion 106 are such that the seal anchor 100 cannot be inserted within tissue tract 12. However, the seal anchor 100 may transition to a compressed condition such that proximal and distal ends 102, 104, as well as intermediate portion 106 are dimensioned for insertion into tissue tract 12.

To facilitate the transition between an expanded and a compressed condition, the seal anchor 100 may be formed from a compressible material having an internal biasing force such that the seal anchor 100 will transition back to an expanded condition upon insertion of the seal anchor 100 within tissue tract 12, thereby ensuring a seal between the seal anchor 100 and the tissue tract 12. Seal anchor 100 may be formed from a shape memory material, a foam material, or a gel material, or the like, but may also be formed from other materials. In an embodiment, the seal anchor 100 may be formed from a material selected from the group consisting of polyisoprene, urethane, and silicone.

Positioning members 114, 115 of the trailing and leading ends 102, 104, respectively, may engage the walls defining the body cavity of the tissue tract 12 to facilitate securement of seal anchor member 100 within the body tissue. For example, positioning member 114 at leading end 104 may engage the internal peritoneal wall and positioning member 114 adjacent trailing end 102 may engage the outer epidermal tissue adjacent the incision 12 within tissue "T". In another embodiment of seal anchor member 100, one or more additional positioning members 114 may be associated with intermediate portion 106.

The use and function of seal anchor member 100 will be discussed during the course of a typical minimally invasive procedure. Initially, the peritoneal cavity (not shown) is insufflated with a suitable biocompatible gas such as, e.g., $CO_2$ gas, such that the cavity wall is raised and lifted away from the internal organs and tissue housed therein, providing greater access thereto. The insufflation may be performed with an insufflation needle or similar device, as is conventional in the art. Either prior or subsequent to insufflation, a tissue tract 12 is created in tissue "T", the dimensions of which may be varied dependent upon the nature of the procedure.

Figure 3:
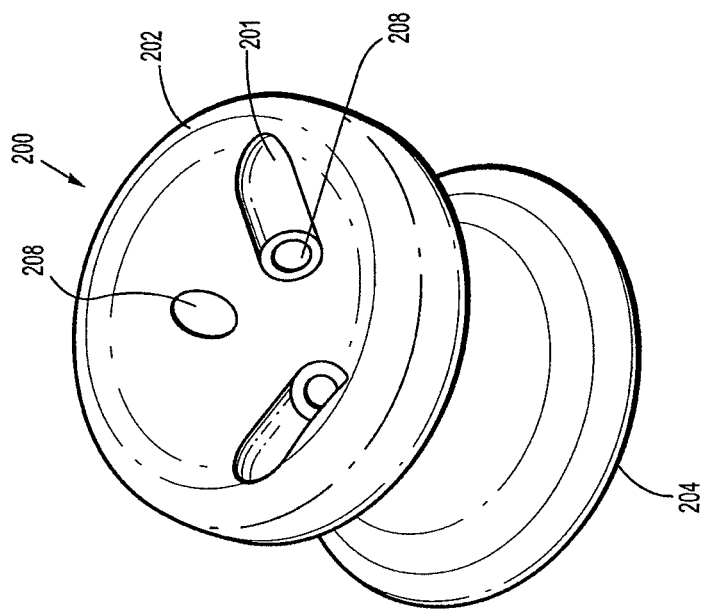
FIG. 3 is another embodiment of a seal anchor in accordance with the present disclosure.

Different embodiments of seal anchors will be described with reference to FIGS. 2 and 3. Seal anchors 200, 300 are substantially similar to seal anchor 100, except in the configuration of lumens and further include structures to stabilize instrumentation inserted within the lumens. Both seal anchor 200 and seal anchor 300, shown in FIGS. 2 and 3, include lumens defining intersecting axes. Seal anchor 200 includes a trailing end 202 and a distal end 204. A plurality of lumens 208 is disposed between the trailing and leading ends 202, 204. Lumens 208 define openings in the trailing end 202 that are radially positioned along the trailing end 202. A cut-out or groove 201 in the leading end extending outward from at least one lumen 208 facilitates stabilization of instrumentation inserted within the lumen 208.

Figure 4:
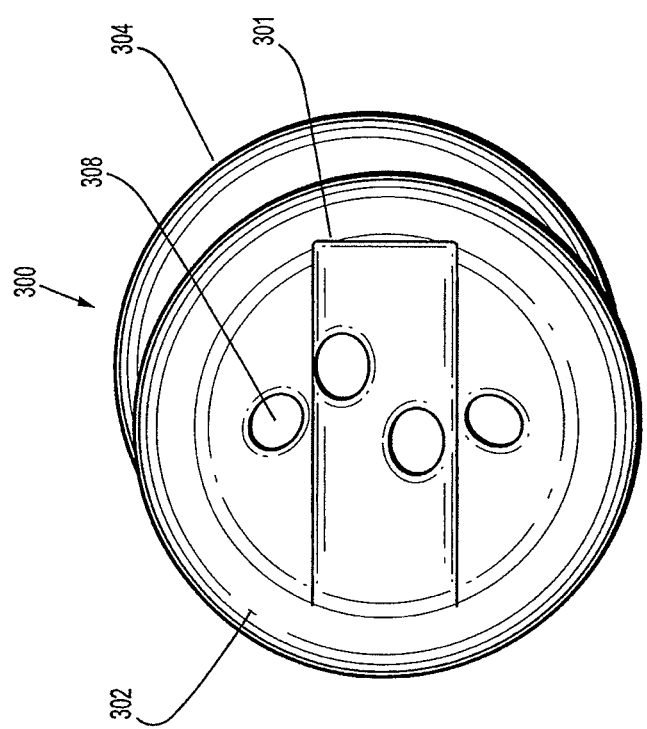
FIG. 4 is a yet another embodiment of a seal anchor in accordance with the present disclosure.

In an alternative embodiment, a seal anchor 300 including plurality of lumens disposed between leading and trailing ends 302, 304 is shown in FIG. 4. A cut-out or groove 301 in an arcuate or half-cylindrical configuration is disposed in the trailing end. At least one lumen 308 is disposed within the groove 301. Groove 301 is adapted to facilitate stabilization of instrumentation inserted within the at least one of the lumens 308 that is disposed within the area defined by the groove 301.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical device comprising:
a compressible housing defining a longitudinal axis, the compressible housing having arcuate leading and trailing ends;
the compressible housing defining a plurality of lumens extending between the leading and trailing ends, each lumen defining an axis, wherein at least a portion of each lumen is adapted to expand to accommodate an instrument in a substantially sealed manner, and wherein, in an at-rest condition, the axis of a first and the axis of a second lumen are nonparallel with respect to each other and with respect to the longitudinal axis of the compressible housing and a third lumen is parallel to the longitudinal axis of the compressible housing;
the compressible housing comprising a leading structure defined in at least one of the leading and trailing ends of the compressible housing, the leading structure extending linearly outward from at least one of proximal and distal ends of two of the plurality of lumens, the leading structure configured to lead an instrument into one of the two of the plurality of lumens, wherein the leading structure extends outward from the two of the plurality of lumens.

2. The surgical device of claim 1, wherein the compressible housing comprises an intermediate portion having a proximal section that tapers inwardly in a distal direction and a distal section that tapers outwardly in the distal direction.

3. The surgical device of claim 1, wherein the leading structure is at least one of a groove and a cut-out.

4. The surgical device of claim 1, wherein the compressible housing is formed from at least one of a foam and a gel.

5. The surgical device of claim 4, wherein the compressible housing is formed from polyisoprene, urethane or silicone.

6. The surgical device of claim 1, wherein the compressible housing is configured to help maintain insufflation pressure in a body cavity during a minimally invasive laparoscopic surgical procedure.

7. The surgical device of claim 1, further comprising an insufflation tube.

* * * * *